(12) United States Patent
Sada et al.

(10) Patent No.: US 7,598,207 B2
(45) Date of Patent: Oct. 6, 2009

(54) HERBICIDAL COMPOSITION

(75) Inventors: Yoshinao Sada, Funabashi (JP); Satoru Kizawa, Kakogawa (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/785,679

(22) Filed: Apr. 19, 2007

(65) Prior Publication Data
US 2007/0254810 A1 Nov. 1, 2007

(30) Foreign Application Priority Data
Apr. 28, 2006 (JP) ............... 2006-125006

(51) Int. Cl.
*A01N 33/00* (2006.01)
*A01N 33/08* (2006.01)
*A01N 41/06* (2006.01)
*A01N 65/00* (2006.01)

(52) U.S. Cl. ............ 504/118; 504/149; 504/215; 504/243

(58) Field of Classification Search ............ 504/243, 504/118, 215, 149
See application file for complete search history.

(56) References Cited

U.S. PATENT DOCUMENTS

| 6,498,126 B1 | 12/2002 | Hacker et al. |
| 2005/0032650 A1 | 2/2005 | Tanaka et al. |
| 2005/0250647 A1 | 11/2005 | Hills et al. |

FOREIGN PATENT DOCUMENTS

EP 1466527 A1 10/2004

JP 2005-126415 A 5/2005

OTHER PUBLICATIONS

Flumioxazin, California Department of Pesticide Regulation Public Report Jun. 2003, 2003,pp. 1-6.*
Flumioxazin; Notice of Filing a Pesticide petition to Establish a Tolerance for a Certain Pesticide Chemical in or on Food [online], EPA Federal Register , Mar. 17, 2004, [retrieved Sep. 14, 2008]. Retrieved from the Internet:<URL: http://www.fluoridealert.org/pesticides/flumioxazin.fr.mar.17.2004.htm> pp. 1-8.*
Partial English language translation of JP 2005126415 A (May 19, 2005).
English language abstract of JP 2032005 A (Feb. 1, 1990).

* cited by examiner

*Primary Examiner*—Johann R Richter
*Assistant Examiner*—Andriae M Holt
(74) *Attorney, Agent, or Firm*—Birch, Stewart, Kolasch & Birch, LLP

(57) ABSTRACT

A herbicidal composition which comprises N-(7-fluoro-3,4-dihydro-3-oxo-4-prop-2-ynyl-2H-1,4-benzoxadin-6-yl)cyclohex-1-ene-1,2-dicarboxamide (flumioxazin) and a compound represented by the formula (I):

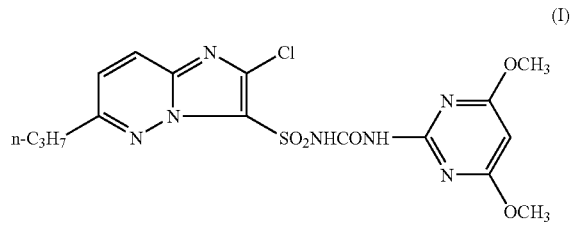

as active ingredients, wherein the weight ratio of flumioxazin:Compound [I] is 1:0.01-1:100, has an excellent herbicidal activity for controlling weeds in crop fields, vegetable fields, tree land or non-cultivated land, and causes no phytotoxicity against useful plants.

11 Claims, No Drawings

HERBICIDAL COMPOSITION

TECHNICAL FIELD

This invention directs to a herbicidal composition and a herbicidal method.

BACKGROUND ART

At the present time, numerous herbicides are commercially available and they are widely used. There are, however, a wide variety of weeds to be controlled and their growth extends over a long time. For this reason, the requested are herbicides with higher herbicidal activity, a wide weed control spectrum, long term effect, and safety to crops.

DISCLOSURE OF THE INVENTION

This invention provides a composition and method for controlling a wide variety of weeds with higher herbicidal effect without phytotoxicity to crops.

Namely, the invention provides a herbicidal composition which comprises N-(7-fluoro-3,4-dihydro-3-oxo-4-prop-2-ynyl-2H-1,4-benzoxadin-6-yl) cyclohex-1-ene-1,2-dicarboxamide (flumioxazin) and a compound represented by the formula (I):

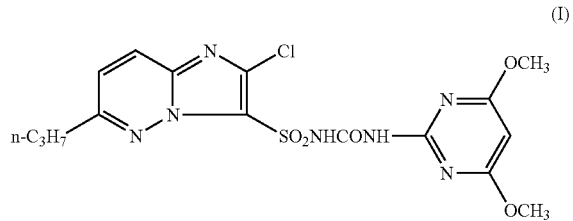

(Compound [I]) as active ingredients, wherein the weight ratio of flumioxazin:Compound [I] is 1:0.01-1:100.

Further, it provides a herbicidal method which comprises applying flumioxazin and Compound [I] to weeds or soil in a place where the weeds grow or will grow, wherein the weight ratio of flumioxazin:Compound [I] is 1:0.01-1:100.

Flumioxazin [Chemical name: N-(7-fluoro-3,4-dihydro-3-oxo-4-prop-2-ynyl-2H-1,4-benzoxadin-6-yl)cyclohex-1-ene-1,2-dicarboxamide] is a herbicidally active compound described in Crop Protection Handbook Vol. 89 (2003), Meister Publishing Company, ISBN: 1-892829-06-1, page C-236. It can be prepared by a known production method, and the formulations containing flumioxazin are available on the market.

Compound [I] can be prepared by a known production method described in USP 2005-0032650A.

The herbicidal composition of the present invention comprises flumioxazin and Compound [I] as active ingredients and the ratio of flumioxazin:Compound [I] in the herbicidal composition is 1:0.01-1:100, preferably 1:0.1-1:20, more preferably 1:0.2-1:10 by weight.

The herbicidal composition has herbicidal activity against a wide variety of weeds, and thus, can be used for controlling a wide variety of weeds effectively in the fields where crops are cultivated with or without tillage, vegetable field, tree land or non-cultivated land. Further, it does not cause significant phytotoxicity to useful plants.

The present invention also provides a method for controlling weeds which comprises applying jointly or simultaneously flumioxazin and Compound [I] to weeds or soil in a place where the weeds grow or will grow, wherein the ratio of flumioxazin:Compound [I] is 1:0.01-1:100, preferably 1:0.1-1:20, more preferably 1:0.2-1:10 by weight.

The method can be used for controlling weeds, especially in crop fields, vegetable fields, tree land or non-cultivated land.

Examples of the crop field in the present invention include the fields of edible crops such as peanut, soybean, corn, wheat and barley; feed crops such as sorghum and oat; industrial crops such as cotton; and sugar crops such as sugarcane. Examples of the vegetable field in the present invention include the fields of Solanaceae vegetables such as eggplant, tomato, green pepper, red pepper and potato; Cucurbitaceae vegetables such as cucumber, pumpkin, zucchini, watermelon and melon; Brassicaceae vegetables such as radish, turnip, horseradish, cohlrabi, Chinese cabbage, cabbage, leaf mustard, broccoli and cauliflower; Compositae vegetables such as burdock, crown daisy, artichoke and lettuce; Liliaceae vegetables such as leek, onion, garlic and asparagus; Umbelliferae vegetables such as carrot, parsley, celery and parsnip; Chenopodiaceae vegetables such as spinach and chard; Lamiacea vegetables such as perilla, mint, basil and lavender; strawberry; sweet potato; yam; and taro. Examples of the tree land include orchards, a tea plantation, a mulberry field, a coffee plantation, a banana plantation, a palm plantation, flower tree land, a flower field, nursery tree land, young plant land, a forest and a garden. Examples of the orchard include pome fruits such as apple, pear, Japanese pear, Chinese quince and quince; stone fruits such as peach, plum, nectarine, Japanese apricot, cherry, apricot and prune; citrus such as Satsuma orange, orange, lemon, lime and grapefruit; tree nuts such as chestnut, walnut, hazel, almond, pistachio, cashew and macadamia; berries such as blueberry, cranberry, blackberry and raspberry; grapes; persimmon; olive; and loquat. Examples of the non-cultivated land in the present invention include a playground, vacant land, a neighborhood of railroad, a park, a car park, a neighborhood of road, a dry riverbed, land under power-transmission lines, land for housing and a site for a factory.

Examples of the weeds include:

Polygonaceae weeds such as *Polygonum convolvulus* (wild buckwheat), *Polygonum lapathifolium* (pale smartweed), *Polygonum pensylvanicum* (Pennsylvania smartweed), *Polygonum persicaria* (ladysthumb), *Rumex crispus* (curly dock), *Rumex obtusifolius* (European dock) and *Polygonum cuspidatum* (Japanese knotweed);

Portulacaceae weeds such as *Portulaca oleracea* (common purslane);

Caryophyllaceae weeds such as *Stellaria media* (common chickweed);

Chenopodiaceae weeds such as *Chenopodium album* (common lambsquarters) and *Kochia scoparia* (fireweed);

Amaranthaceae weeds such as *Amaranthus retroflexus* (redroot pigweed) and *Amaranthus hybridus* (smooth pigweed);

Cruciferae weeds such as *Raphanus raphanistrum* (wild radish), *Sinapis arvensis* (wild mustard) and *Capsella bursa-pastoris* (shepherdspurse);

Leguminosae weeds such as *Sesbania exaltata* (hemp sesbania), *Cassia obtusifolia* (sicklepod), *Desmodium tortuosum*

(Florida beggarweed), *Trifolium repens* (white clover), *Pueraria lobata* (arrowroot) and *Vicia angustifolia* (common vetch);

Malvaceae weeds such as *Abutilon theophrasti* (velvetleaf and *Sida spinosa* (prickly sida);

Violaceae weeds such as *Viola arvensis* (field pansy) and *Viola tricolor* (wild pansy);

Rubiaceae weeds such as *Galium aparine* (cleavers);

Convolvulaceae weeds such as *Ipomoea hederacea* (ivyleaf morningglory), *Ipomoea purpurea* (tall morningglory), *Ipomoea hederacea* var *integriuscula* (entireleaf morningglory), *Ipomoea lacunose* (pitted morningglory) and *Convolvulus arvensis* (field bindweed);

Labiatae weeds such as *Lamium purpureum* (purple deadnettle) and *Lamium amplexicaule* (henbit);

Solanaceae weeds such as *Datura stramonium* (jimsonweed) and *Solanum nigrum* (black nightshade);

Scrophulariaceae weeds such as *Veronica persica* (Persian speedwell) and *Veronica hederaefolia* (ivyleaf speedwell);

Compositae weeds such as *Xanthium pensylvanicum* (common cocklebur), *Helianthus annuus* (common sunflower), *Matricaria inodora* (scentless chamomile), *Chrysanthemum segetum* (corn marigold), *Matricaria matricarioides* (pineappleweed), *Ambrosia artemisiifolia* (common ragweed), *Ambrosia trifida* (giant ragweed), *Erigeron Canadensis* (horseweed), *Artemisia princes* (Japanese mugwort) and *Solidago altissima* (tall goldenrod);

Boraginaceae weeds such as *Myosotis arvensis* (forget-me-not);

Asclepiadaceae weeds such as *Asclepias syriaca* (common milkweed);

Euphorbiaceae weeds such as *Euphorbia helioscopia* (sun spurge) and *Euphorbia maculata* (spotted spurge);

Geraniaceae weeds such as *Geranium carolinense* (Carolina geranium) and *Erodium cicutarium;*

Gramineae weeds such as *Echinochloa crus-galli* (barnyardgrass), *Setaria viridis* (green foxtail), *Setaria faberi* (giant foxtail), *Digitaria sanguinalis* (southern crabgrass), *Eleusine indica* (goosegrass), *Poa annua* (annual bluegrass), *Alopecurus myosuroides* (blackgrass), *Avena fatus* (wild oats), *Sorghum halepense* (Johnsongrass), *Agropyron repens* (quackgrass), *Bromus tectorum* (downy brome), *Cynodone dactylon* (Bermudagrass), *Panicum dichotomiflorum* (fall panicum), *Panicum texanum* (Texas panicum), *Sorghum vulgare* (shattercane) and *Lolium multiflorum* (Italian ryegrass);

Commelinaceae weeds such as *Commelina communis* (Asiatic dayflower) and *Commelina benghalensis* (Bengal dayflower);

Equisetaceae weeds such as *Equisetum arvense* (field horsetail); and

Cyperaceae weeds such as *Cyperus iria* (rice flatsedge), *Cyperus rotundus* (purple nutsedge) and *Cyperus esculentus* (yellow nutsedge).

The herbicidal composition can be formulated to emulsifiable concentrates, wettable powders, suspensible concentrates, granules and so on by mixing a solid carrier or a liquid carrier and optionally surfactants and the other auxiliaries for formulation. These formulations generally contain about 0.1 to 90% by weight, preferably about 1 to 80% by weight of the total amount of flumioxazin and Compound [I].

Examples of the solid carrier used for formulating the composition of the invention include fine powders and granules of clays such as kaolinite, diatomaceous earth, synthetic hydrated silica, Fubasami clay, bentonite and terra alba; talc; the other inorganic minerals such as sericite, quartz powder, sulfur powder, activated carbon and calcium carbonate; and chemical fertilizer such as ammonium sulfate, ammonium phosphate, ammonium nitrate, ammonium chloride and urea. Examples of the liquid carrier include water; alcohols such as methanol and ethanol; ketones such as acetone, methyl ethyl ketone and cyclohexanone; aromatic hydrocarbons such as toluene, xylene, ethylbenzene and methylnaphthalene; non-aromatic hydrocarbons such as hexane, cyclohexane and kerosene; esters such as ethyl acetate and butyl acetate; nitriles such as acetonitrile and isobutyronitrile; ethers such as dioxane and diisopropyl ether; acid amides such as dimethylformamide and dimethylacetamide; halogenated hydrocarbons such as dichloroethane and trichloroethylene.

Examples of the surfactant used for formulation include alkyl sulfate esters, alkylsulfonate salts, alkylarylsulfonate salts, alkylaryl ethers, polyoxyethylene alkylaryl ethers, polyethylene glycol ethers, polyvalent alcohol esters and sugar alcohol derivatives. Examples of the other auxiliary for formulation include sticking agents and dispersants such as casein; gelatin; polysaccharide (e.g., starch, gum arabic, cellulose derivatives, alginic acid); lignin derivatives; bentonite; and synthetic water-soluble polymers (e.g., polyvinyl alcohol, polyvinylpyrrolidone, polyacrylic acid); and stabilizers such as PAP (isopropyl acid phosphate), BHT (2,6-tert-butyl-4-methylphenol), BHA (2-/3-tert-butyl-4-methoxyphenol), vegetable oil, mineral oil, fatty acid and fatty acid ester.

The herbicidal composition can also be prepared by mixing each formulation after formulating each of the active ingredients with the above-mentioned procedure.

The herbicidal composition obtained above can be applied as it is for the herbicidal method of the present invention. Further, it can be diluted with water or the like, and then the dilution can be applied to soil or a plant. It may be expected to increase the herbicidal effect by using the herbicidal composition of the invention together with another herbicide. Moreover, the herbicidal composition can be used with insecticides, fungicides, plant growth regulators, fertilizers, safeners, soil-improving agents and so on.

The dosage of the herbicidal composition or method depends on the mixing ratio of flumioxazin and Compound [I] as active ingredients, weather condition, formulation types, application time, application methods, application places, objective weeds and crops, and it is usually about 1 to 1000 g of the total amount of the active ingredients per hectare. When the formulation is emulsifiable concentrate, wettable powder, suspensible concentrate, the designated amount is usually diluted with about 100 to 2000 liters of water per hectare and applied. Further, when the composition of the invention is applied to weeds by foliar treatment, it is expected to increase herbicidal effect against weeds by adding an adjuvant to the dilution of the composition of the invention.

EXAMPLES

Hereinafter, the present invention is explained by examples in detail.

Formulation examples are given below. In the following examples, part(s) means part(s) by weight.

Formulation Example 1

Twenty-five parts of flumioxazin, 25 parts of Compound [I], 3 parts of calcium ligninsulfonate, 2 parts of sodium laurylsulfate and 45 parts of synthetic hydrated silica are well pulverized and mixed to give wettable powder.

Formulation Example 2

Seventy parts of flumioxazin, 14 parts of Compound [I], 3 parts of calcium ligninsulfonate, 2 parts of sodium laurylsulfate and 11 parts of synthetic hydrated silica are well pulverized and mixed to give wettable powder.

Formulation Example 3

Fourteen parts of flumioxazin, 70 parts of Compound [I], 3 parts of calcium ligninsulfonate, 2 parts of sodium laurylsulfate and 11 parts of synthetic hydrated silica are well pulverized and mixed to give wettable powder.

Formulation Example 4

Ten parts of flumioxazin, 5 parts of Compound [I], 3 parts of calcium ligninsulfonate, 2 parts of sodium laurylsulfate and 80 parts of synthetic hydrated silica are well pulverized and mixed to give wettable powder.

Formulation Example 5

Twenty parts of flumioxazin, 20 parts of Compound [I], 3 parts of polyoxyethylene sorbitan monooleate, 3 parts of CMC (carboxymethylcellulose) and 54 parts of water are mixed and wet-pulverized to make the particle diameter to $5\mu$ or less to give suspensible concentrate.

Formulation Example 6

Fifty parts of flumioxazin, 10 parts of Compound [I], 3 parts of polyoxyethylene sorbitan monooleate, 3 parts of CMC (carboxymethylcellulose) and 34 parts of water are mixed and wet-pulverized to make the particle diameter to $5\mu$ or less to give suspensible concentrate.

Formulation Example 7

Five parts of flumioxazin, 25 parts of Compound [I], 3 parts of polyoxyethylene sorbitan monooleate, 3 parts of CMC (carboxymethylcellulose) and 64 parts of water are mixed and wet-pulverized to make the particle diameter to $5\mu$ or less to give suspensible concentrate.

Formulation Example 8

Four parts of flumioxazin, 2 parts of Compound [I], 3 parts of polyoxyethylene sorbitan monooleate, 3 parts of CMC (carboxymethylcellulose) and 88 parts of water are mixed and wet-pulverized to make the particle diameter to $5\mu$ or less to give suspensible concentrate.

Formulation Example 9

One part of flumioxazin, one part of Compound [I], 0.5 part of Neocol YSK (sodium dialkylsulfosuccinate ester produced by Dai-ichi Kogyo Seiyaku Co., Ltd.), 2 parts of Toxanon GR31A (anionic polycarboxylate surfactant produced by Sanyo Chemical Industries, Ltd.), 30 parts of Kunigel V1 (bentonite produced by Kuminime Industries Co., Ltd.) and 65.5 parts of calcium carbonate are charged into a small kneader, mixed, kneaded, granulated with an extruder (RG-5M manufactured by Kikusui Seisakusho, Ltd.) and dried with a fluidized bed dryer (MDB-400 manufactured by Fuji Paudal Co., Ltd.), and then filtered with 16-48 mesh to give granules.

Biological test is given below.

Valuation Basis

The herbicidal activity is evaluated at 11 levels using the indices of 0 to 10, i.e., shown by 0, 1, 2, 3, 4, 5, 6, 7, 8, 9 or 10, wherein a score of "0" means that there is no or little difference in the degree of growth between treated plants and untreated plants at the time of observation and a score of "10" means that the test plants die completely or their growth is completely inhibited. The herbicidal values of "7", "8", "9" and "10" show excellent herbicidal activity, and the value "6" or less shows insufficient herbicidal activity. The phytotoxicity against crops is evaluated by using "no damage", "small", "medium" or "severe", wherein "no damage" means that no or little damage is found, "small" means that the damage is light, "medium" means that the damage is medium and "severe" means that severe damage is found.

Test Example 1

Plastic pots each having a diameter of 18 cm and a height of 14 cm were filled with upland soil, and then seeded with wheat and barnyardgrass. On the surface of the soil of the above-mentioned plastic pots, Flumioxazin granules (granules containing 0.25% of flumioxazin, commercial name: Broad Star, produced by Valent U.S.A.), granules containing Compound [I] (prepared by using one part of Compound [I], 0.5 part of Neocol YSK, 2 parts of Toxanon GR31A, 30 parts of Kunigel VI and 66.5 parts of calcium carbonate according to Formulation example 9), and a mixture of the Flumioxazin granules with the granules containing Compound [I] were applied with hand in a designated amount given by Table 1.

The treated plants were grown in the greenhouse. The herbicidal activity and phytotoxicity against the crop were examined 48 days after the application. The results are shown in Table 1.

TABLE 1

| Test compound | Amount of active ingredient (g/ha) | Herbicidal activity Barnyardgrass | Phytotoxicity against crop Wheat |
|---|---|---|---|
| flumioxazin | 40 | 4 | No damage |
| Compound [I] | 50 | 0 | No damage |
| | 100 | 2 | No damage |
| flumioxazin + | 40 + 50 | 7 | No damage |
| Compound [I] | 40 + 100 | 10 | No damage |

As shown in Test example 1, excellent herbicidal effect was synergistically provided in the area treated with the composition of the invention compared to the area treated with flumioxazin or Compound [I] solely. Further, there was no damage found in wheat.

Test Example 2

Plastic pots each having a diameter of 9 cm and a height of 7 cm were filled with upland soil, and then seeded with peanut. Next day, a mixture of Flumioxazin WDG (water dispersible granules containing 51% of flumioxazin, commercial name: Valor SX, produced by Valent U.S.A.) and emulsifiable concentrate containing Compound [I] (prepared by dissolving Compound [I] with acetone containing Tween 20 (surfactant, sorbitan monolaurate polyglycol ether)) was diluted with a designated amount of water, and applied uniformly on the surface of the soil with a small sprayer.

The treated plants were grown in the greenhouse. The herbicidal activity and phytotoxicity against the crop were examined 21 days after the application. The results are shown in Table 2.

TABLE 2

| Test compound | Amount of active ingredient (g/ha) | Phytotoxicity against crop Peanut |
|---|---|---|
| flumioxazin + Compound [I] | 25 + 50 | No damage |
| | 50 + 50 | No damage |
| | 100 + 100 | No damage |

As shown in Test example 2, the composition of the invention caused no or little damage against peanut.

Test Example 3

Plastic pots each having a width of 32 cm, a depth of 22 cm and a height of 8 cm were filled with upland soil, and then planted with a tuber of yellow nutsedge. Next day, Flumioxazin WDG (water dispersible granules containing 51% of flumioxazin, commercial name: Valor SX, produced by Valent U.S.A.), emulsifiable concentrate containing Compound [I] (prepared by dissolving Compound [I] with acetone containing Tween 20 (surfactant, sorbitan monolaurate polyglycol ether)) and a mixture thereof was diluted with a designated amount of water, and applied uniformly on the surface of the soil with a small sprayer.

The treated plants were grown in the greenhouse. The herbicidal activity and phytotoxicity against the crop were examined 21 days after the application. The results are shown in Table 3.

TABLE 3

| Test compound | Amount of active ingredient (g/ha) | Herbicidal activity Yellow nutsedge |
|---|---|---|
| flumioxazin | 25 | 0 |
| | 50 | 1 |
| Compound [I] | 100 | 7 |
| flumioxazin + Compound [I] | 25 + 100 | 9 |
| | 50 + 100 | 10 |

As shown in Test example 3, excellent herbicidal effect was synergistically provided in the area treated with the composition of the invention compared to the area treated with flumioxazin or Compound [I] solely.

Test Example 4

Plastic pots each having a width of 32 cm, a depth of 22 cm and a height of 8 cm were filled with upland soil, and then transplanted with tomato and seeded with crabgrass and redroot pigweed. Next day, a mixture of Flumioxazin WDG (water dispersible granules containing 51% of flumioxazin, commercial name: Valor SX, produced by Valent U.S.A.) and emulsifiable concentrate containing Compound [I] (prepared by dissolving Compound [I] with acetone containing Tween 20 (surfactant, sorbitan monolaurate polyglycol ether)) was diluted with a designated amount of water, and applied uniformly on the surface of the soil with a small sprayer.

The treated plants were grown in the greenhouse. The herbicidal activity and phytotoxicity against the vegetable were examined 21 days after the application. The results are shown in Table 4.

TABLE 4

| Test compound | Amount of active ingredient (g/ha) | Herbicidal activity | | Phytotoxicity against vegetable Tomato |
|---|---|---|---|---|
| | | Crabgrass | Redroot pigweed | |
| flumioxazin + Compound [I] | 25 + 50 | 9 | 10 | No damage |
| | 50 + 50 | 10 | 10 | No damage |
| | 100 + 50 | 10 | 10 | No damage |
| | 25 + 100 | 9 | 10 | No damage |
| | 50 + 100 | 10 | 10 | No damage |
| | 100 + 100 | 10 | 10 | No damage |
| | 25 + 200 | 9 | 10 | No damage |
| | 50 + 200 | 10 | 10 | No damage |
| | 100 + 200 | 10 | 10 | No damage |

As shown in Test example 4, excellent herbicidal effect was provided in the area treated with the composition of the invention. Further, there was no damage found in tomato.

Test Example 5

Plastic pots each having a width of 17 cm, a depth of 12 cm and a height of 7 cm were filled with upland soil, and then transplanted with cucumber and seeded with barnyardgrass, black nightshade and common purslane. Next day, a mixture of Flumioxazin WDG (water dispersible granules containing 51% of flumioxazin, commercial name: Valor SX, produced by Valent U.S.A.) and emulsifiable concentrate containing Compound [I] (prepared by dissolving Compound [I] with acetone containing Tween 20 (surfactant, sorbitan monolaurate polyglycol ether)) was diluted with a designated amount of water, and applied uniformly on the surface of the soil with a small sprayer.

The treated plants were grown in the greenhouse. The herbicidal activity and phytotoxicity against the vegetable were examined 21 days after the application. The results are shown in Table 5.

TABLE 5

| Test compound | Amount of active ingredient (g/ha) | Herbicidal activity | | | Phytotoxicity against vegetable Cucumber |
|---|---|---|---|---|---|
| | | Barnyard grass | Black nightshade | common purslane | |
| flumioxazin + Compound [I] | 25 + 50 | 10 | 10 | 10 | No damage |
| | 50 + 50 | 9 | 10 | 10 | No damage |
| | 25 + 100 | 10 | 10 | 10 | No damage |
| | 50 + 100 | 10 | 10 | 10 | No damage |
| | 25 + 200 | 10 | 10 | 10 | No damage |
| | 50 + 200 | 10 | 10 | 10 | No damage |

As shown in Test example 5, excellent herbicidal effect was provided in the area treated with the composition of the invention. Further, there was no damage found in cucumber.

Test Example 6

Plastic pots each having a diameter of 21 cm and a height of 20 cm were filled with upland soil, and then planted with potato and seeded with barnyardgrass, crabgrass and ivyleaf morningglory. Next day, on the surface of the soil of the above-mentioned plastic pots, Flumioxazin granules (granules containing 0.25% of flumioxazin, commercial name: Broad Star, produced by Valent U.S.A.), granules containing 0.9% of Compound [I] (prepared according to Formulation example 9), and a mixture of the Flumioxazin granules with the granules containing Compound [I] were applied with hand in a designated amount given by Table 6.

The herbicidal activity and phytotoxicity against the vegetable were examined 14 days after the application. The results are shown in Table 6.

TABLE 6

| Test compound | Amount of active ingredient (g/ha) | Herbicidal activity | | | Phytotoxicity against vegetable Potato |
|---|---|---|---|---|---|
| | | Barnyard grass | Crab-grass | Ivyleaf morningglory | |
| flumi-oxazin | 25 | 1 | 5 | 1 | No damage |
| Compound [I] | 100 | 0 | 5 | 1 | No damage |
| flumi-oxazin + Compound [I] | 25 + 100 | 8 | 10 | 7 | No damage |

As shown in Test example 6, excellent herbicidal effect was synergistically provided in the area treated with the composition of the invention. Further, there was no damage found in potato.

Test Example 7

Plastic container having a width of about 46 cm, a depth of about 31 cm and a height of about 26 cm were filled with upland soil and planted with grape (variety: Delaware), and then seeded with barnyardgrass, crabgrass and redroot pigweed. On the surface of the soil of the above-mentioned plastic pots, a mixture of Flumioxazin granules (granules containing 0.25% of flumioxazin, commercial name: Broad Star, produced by Valent U.S.A.) and granules containing 0.9% of Compound [I] (prepared according to Formulation example 9) was applied with hand in a designated amount.

The herbicidal activity and phytotoxicity against the grape were examined 14 days after the application. The results are shown in Table 7.

TABLE 7

| Test compound | Amount of active ingredient (g/ha) | Herbicidal activity | | | Phytotoxicity against grape Grape |
|---|---|---|---|---|---|
| | | Barnyard grass | Crabgrass | Redroot pigweed | |
| flumioxazin + Compound [I] | 200 + 50 | 10 | 10 | 10 | No damage |

As shown in Test example 7, excellent herbicidal effect was provided in the area treated with the composition of the invention. Further, there was no damage found in grape.

Test Example 8

Plastic container having a width of about 46 cm, a depth of about 31 cm and a height of about 26 cm were filled with upland soil and planted with a chestnut tree (variety: Ginyose), and then seeded with barnyardgrass, crabgrass and redroot pigweed. On the surface of the soil of the above-mentioned plastic pots, a mixture of Flumioxazin granules (granules containing 0.25% of flumioxazin, commercial name: Broad Star, produced by Valent U.S.A.) and granules containing 0.9% of Compound [I] (prepared according to Formulation example 9) was applied with hand in a designated amount.

The herbicidal activity and phytotoxicity against the chestnut were examined 14 days after the application. The results are shown in Table 8.

TABLE 8

| Test compound | Amount of active ingredient (g/ha) | Herbicidal activity | | | Phytotoxicity against chestnut Chestnut |
|---|---|---|---|---|---|
| | | Barnyard grass | Crabgrass | Redroot pigweed | |
| flumioxazin + Compound [I] | 40 + 200 | 10 | 10 | 10 | No damage |

As shown in Test example 8, excellent herbicidal effect was provided in the area treated with the composition of the invention. Further, there was no damage found in chestnut.

The present invention makes it possible to control various weeds at a low dosage in crop fields, vegetable fields, tree land, non-cultivated land and so on.

What is claimed is:

1. A herbicidal composition which comprises N-(7-fluoro-3,4-dihydro-3-oxo-4-prop-2-ynyl-2H-1,4-benzoxadin-6-yl) cyclohex-1-ene-1,2-dicarboxamide (flumioxazin) and a compound represented by the formula (I):

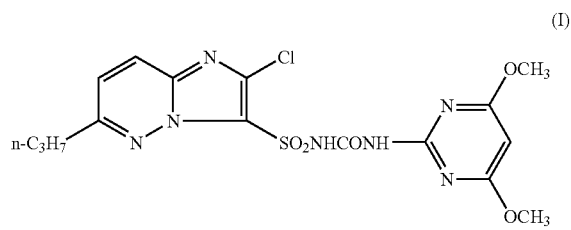

(Compound [I]) as active ingredients, wherein the weight ratio of flumioxazin:Compound [I] is 1:0.2-1:10.

2. A method for controlling weeds which comprises applying N-(7-fluoro-3,4-dihydro-3-oxo-4-prop-2-ynyl-2H-1,4-benzoxadin-6-yl)cyclohex-1-ene-1,2-dicarboxamide and a compound represented by the formula (I) jointly or simultaneously to weeds or soil in a place where the weeds grow or will grow, wherein the weight ratio of flumioxazin:Compound [I] is 1:0.2-1:10

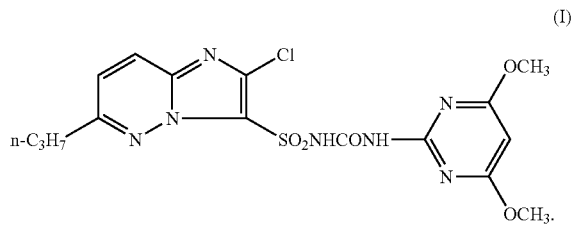

(I)

3. The method for controlling weeds according to claim 2, wherein the weeds are in crop fields, vegetable fields, tree land or non-cultivated land.

4. The method for controlling weeds according to claim 2, wherein the weeds are in crop fields.

5. The method for controlling weeds according to claim 2, wherein the weeds are in wheat fields.

6. The method for controlling weeds according to claim 2, wherein the weeds are in peanut fields.

7. The method for controlling weeds according to claim 2, wherein the weeds are in tomato fields.

8. The method for controlling weeds according to claim 2, wherein the weeds are in cucumber fields.

9. The method for controlling weeds according to claim 2, wherein the weeds are in potato fields.

10. The method for controlling weeds according to claim 2, wherein the weeds are in grape fields.

11. The method for controlling weeds according to claim 2, wherein the weeds are in chestnut fields.

* * * * *